(12) United States Patent
Slone et al.

(10) Patent No.: US 7,727,282 B2
(45) Date of Patent: Jun. 1, 2010

(54) METHOD AND APPARATUS FOR IMPLANTING A PROSTHESIS

(75) Inventors: W Jason Slone, Silver Lake, IN (US); Kimberly S Parcher, Etna Green, IN (US); Ryan C Lakin, Newton, NJ (US); Aaron J Smits, Wayne, IN (US); Kurt N Schmidt, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 963 days.

(21) Appl. No.: 11/384,931

(22) Filed: Mar. 17, 2006

(65) Prior Publication Data

US 2007/0219562 A1 Sep. 20, 2007

(51) Int. Cl.
*A61F 2/34* (2006.01)
*A61F 2/46* (2006.01)
*A61B 17/88* (2006.01)

(52) U.S. Cl. .................. 623/22.12; 606/91; 606/99; 623/22.21; 623/22.24

(58) Field of Classification Search .............. 623/22.11, 623/22.21–22.39, 22.12; 606/91, 99
See application file for complete search history.

(56) References Cited

U.S. PATENT DOCUMENTS

| | | | |
|---|---|---|---|
| 3,840,904 A | 10/1974 | Tronzo | |
| 4,101,985 A | 7/1978 | Baumann et al. | |
| 4,123,806 A | 11/1978 | Amstutz et al. | |
| 4,677,972 A | 7/1987 | Tornier | |
| 4,715,860 A | 12/1987 | Amstutz et al. | |
| 4,752,296 A | 6/1988 | Buechel et al. | |
| 5,030,221 A | 7/1991 | Buechel et al. | |
| 5,037,424 A | 8/1991 | Aboczsky | |
| 5,116,339 A | 5/1992 | Glock | |
| 5,169,399 A | 12/1992 | Ryland et al. | |
| 5,171,243 A | 12/1992 | Kashuba et al. | |
| 5,250,051 A | 10/1993 | Maryan | |
| 5,284,483 A | 2/1994 | Johnson et al. | |
| 5,320,625 A | 6/1994 | Bertin | |
| 5,364,403 A | 11/1994 | Petersen et al. | |
| 5,417,696 A | 5/1995 | Kashuba et al. | |
| 5,431,657 A | 7/1995 | Rohr | |
| 5,474,560 A | 12/1995 | Rohr, Jr. | |
| 5,486,181 A | 1/1996 | Cohen et al. | |
| 5,527,317 A | 6/1996 | Ashby et al. | |

(Continued)

OTHER PUBLICATIONS

"Conserve Total 6mm Shell with BFH Technology," Wright Medical Technology, Inc., copyright 2003 (8 sheets).

(Continued)

*Primary Examiner*—David H Willse
*Assistant Examiner*—Megan Wolf
(74) *Attorney, Agent, or Firm*—Harness, Dickey

(57) ABSTRACT

A method and apparatus for implanting various portions of a prosthesis into an anatomy. The instruments can include portions that allow for positive and rigid engagement with a selected prosthesis member to allow for positioning it relative to the anatomy. Further, various instruments can include portions that allow it to engage or match with marking portions or alignment portions on a first prosthesis member to align a second prosthesis member with the first one. Further, methods of using the various instruments are taught and providing for a less or minimally invasive procedure.

30 Claims, 11 Drawing Sheets

U.S. PATENT DOCUMENTS

| | | | |
|---|---|---|---|
| 5,540,697 A | 7/1996 | Rehmann et al. | |
| 5,571,111 A | 11/1996 | Aboczky | |
| 5,571,200 A | 11/1996 | Cohen et al. | |
| 5,571,201 A | 11/1996 | Averill et al. | |
| 5,584,837 A | 12/1996 | Petersen | |
| 5,630,819 A | 5/1997 | Ashby et al. | |
| 5,658,294 A | 8/1997 | Sederholm | |
| 5,683,399 A | 11/1997 | Jones | |
| 5,879,402 A | 3/1999 | Lawes et al. | |
| 5,904,688 A | 5/1999 | Gilbert et al. | |
| 5,928,287 A | 7/1999 | Keller | |
| 5,954,727 A | 9/1999 | Collazo | |
| 5,976,148 A | 11/1999 | Charpenet et al. | |
| 6,022,357 A * | 2/2000 | Reu et al. | 606/99 |
| 6,027,505 A | 2/2000 | Peter et al. | |
| 6,063,123 A | 5/2000 | Burrows et al. | |
| 6,063,124 A | 5/2000 | Amstutz | |
| 6,156,069 A | 12/2000 | Amstutz | |
| 6,214,014 B1 | 4/2001 | McGann | |
| 6,231,611 B1 | 5/2001 | Mosseri | |
| 6,264,698 B1 | 7/2001 | Lawes et al. | |
| 6,395,005 B1 | 5/2002 | Lovell | |
| 6,468,281 B1 | 10/2002 | Bädorf et al. | |
| 6,475,243 B1 | 11/2002 | Sheldon et al. | |
| 6,482,237 B2 | 11/2002 | Mosseri | |
| 6,589,284 B1 | 7/2003 | Silberer | |
| 6,626,913 B1 | 9/2003 | McKinnon et al. | |
| 6,682,567 B1 | 1/2004 | Schroeder | |
| 6,695,850 B2 | 2/2004 | Diaz | |
| 6,723,102 B2 | 4/2004 | Johnson et al. | |
| 6,743,235 B2 | 6/2004 | Subba Rao | |
| 6,746,452 B2 | 6/2004 | Tuke et al. | |
| 2002/0082706 A1 | 6/2002 | Raugel | |
| 2002/0177854 A1 | 11/2002 | Tuke et al. | |
| 2003/0050645 A1 | 3/2003 | Parker et al. | |
| 2003/0130741 A1 | 7/2003 | McMinn | |
| 2003/0158559 A1 | 8/2003 | Diaz | |
| 2003/0187512 A1 | 10/2003 | Frederick et al. | |
| 2003/0220698 A1 | 11/2003 | Mears et al. | |
| 2003/0236523 A1 | 12/2003 | Johnson et al. | |
| 2004/0073225 A1 | 4/2004 | Subba Rao | |
| 2004/0073226 A1 | 4/2004 | Cotting et al. | |
| 2004/0153063 A1 | 8/2004 | Harris, Jr. | |
| 2004/0186586 A1 | 9/2004 | Seyer et al. | |
| 2004/0215200 A1 | 10/2004 | Tornier et al. | |
| 2007/0219640 A1 * | 9/2007 | Steinberg | 623/22.12 |

OTHER PUBLICATIONS

"Conserve Total Hip System with BFH Technology," Wright Medical Technology, Inc., copyright 2003 (6 sheets).

"Lineage Acetabular Cup System," Wright Medical Technology, Inc. copyright 2004 (10 sheets).

* cited by examiner

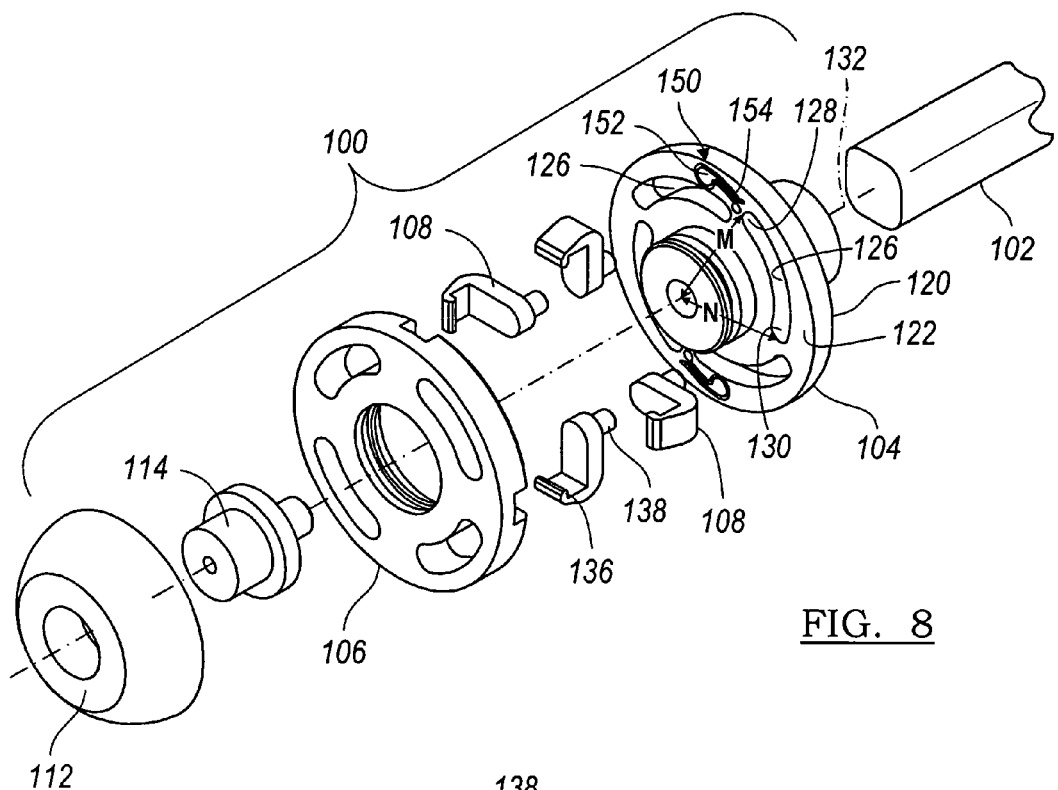
FIG. 8
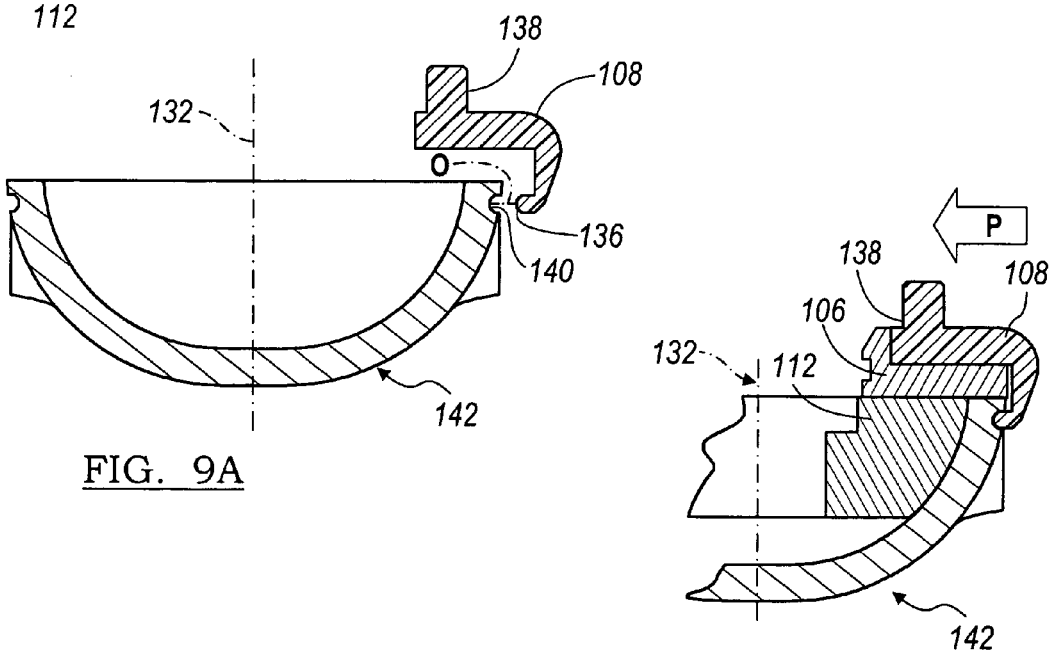
FIG. 9A
FIG. 9B

METHOD AND APPARATUS FOR IMPLANTING A PROSTHESIS

FIELD

The present teachings relate generally to a method and apparatus of positioning an implant in an anatomy, and particularly to a method and apparatus for positioning an implant relative to a joint.

BACKGROUND

A natural anatomy includes several anatomical portions that are generally able to articulate relative to one another in a substantially pain-free and natural manner. For example, a glenoid can articulate with a humerus or an acetabelum can articulate with a femoral head. For various reasons, however, the various anatomical portions may become damaged or not operate in a natural manner. Due to various reasons, for example, injury or disease, the anatomical portions can become damaged. Once an anatomical portion has become damaged, under certain circumstances, a prosthesis can be positioned relative to the remaining anatomical portions to allow for mimicking the natural anatomical motion. For example, an acetabular implant can be positioned relative to an acetabulum, a femoral head implant can be positioned relative to a femur, or other various prosthesis can be positioned in the anatomy to allow for obtaining or repairing natural anatomical motion.

Various anatomical implants can be positioned relative to the anatomy using various procedures. Generally, an open procedure can be used to position a prosthesis relative to the anatomy. In an open procedure, an incision is formed through the soft tissue, which can include adipose tissue, muscle tissue, skin tissue and the like. The open incision allows for access to the entire anatomical area to be replaced, such as a large incision over a substantial portion of the knee joint, the hip joint, or the like. The damaged anatomical portions can then be generally removed to allow for placement of the prosthesis members. In a hip joint, the acetabulum may be reamed and an acetabular implant may be positioned relative to the reamed actabelum.

Generally, an implant may include a portion that allows it to be fixed to the anatomy and a second portion that allows it to articulate with another portion of anatomy or another implant. It may be that the various portions are formed as a single member or formed as multiple members. Nevertheless, the large incision generally allows for ease of access to the natural anatomical portions and for implanting the prosthesis.

It is desirable, however, to allow for the same ease of implantation with use of a smaller incision. A less or minimally invasive procedure can include forming an incision that is only large enough or not substantially larger than the size of the prosthesis or portions of the prosthesis to be implanted in the anatomy. To perform such a procedure, it is desirable to provide instruments that allow for ease of positioning the various portions of the prosthesis and for preparing the anatomy for implantation of the prosthesis while maintaining maximum efficacy of the procedure.

SUMMARY

A method and apparatus for positioning a prosthesis relative to an anatomy through a less invasive incision. The incision can be any appropriate size, such as one that is generally similar to the size of the prosthesis, one that can be expanded to receive the prosthesis, or one that is appropriate for allowing a prosthesis and various instruments to pass through for implanting the prosthesis. Further, various apparatuses are taught that allow for positioning, implanting, and inserting various prostheses relative to an anatomy.

According to various embodiments, an implantation system for positioning a prosthesis system relative to a selected portion of an anatomy including a boney portion is taught. The implantation system can include a shell operable to be positioned relative to the boney portion and a liner to engage an interior portion of the shell. The system can further include a shell inserter instrument operable to engage an exterior engagement portion of the shell to hold the shell in a selected orientation. Also, a liner inserter instrument can hold the liner in a selected orientation and a shell alignment member to engage the shell to orient the liner inserter relative to the shell. The shell and the liner are operable to be positioned relative to the anatomy.

According to various embodiments, an implantation system for positioning a liner prosthesis system relative to a selected portion of the anatomy including a boney portion and a shell prosthesis is disclosed. The implantation system can include a liner prosthesis holding body. A liner engaging member including a finger able to contact the liner prosthesis and moveable between a contacting position and a non-contacting position can be associated with the holding body. A biasing member can bias the finger to the contacting position. A shell prosthesis alignment member may align the liner prosthesis holding body relative to the shell prosthesis. Also, a disengagement member can assist in moving the finger from the contacting position to the non-contacting position.

According to various embodiments, an implantation system for positioning a shell prosthesis system relative to a selected portion of the anatomy including a boney portion is disclosed. The implantation system can include a top plate that defines a track. An engagement member can include an engagement finger and a cam engaging portion able to be positioned in the track. A shell contacting portion can contact the prosthesis system. Also, a handle can rotate the top plate to move the engagement member.

Further areas of applicability of the present teachings will become apparent from the detailed description provided hereinafter. It should be understood that the detailed description and various embodiments are intended for purposes of illustration only and are not intended to limit the scope of the teachings.

BRIEF DESCRIPTION OF THE DRAWINGS

The present teachings will become more fully understood from the detailed description and the accompanying drawings, wherein:

FIG. 8 is an exploded perspective view of an acetabular shell inserter assembly;

FIG. 9A is a detailed cross-sectional view of an acetabular shell inserter assembly preparing to engage an acetabular shell according to various embodiments;

FIG. 9B is a detailed cross-sectional view of an acetabular shell assembly inserter engaging an acetabular shell;

DETAILED DESCRIPTION OF THE VARIOUS EMBODIMENTS

The following description of the various embodiments is merely exemplary in nature and is in no way intended to limit the teachings, its application, or uses. It will be understood that the following teachings may be applied to any appropriate procedure for an anatomy or a prosthesis to be implanted into an anatomy. Although the following teachings relate generally to a prosthesis to replace an acetabulum, it will be understood that the various teachings, including the apparatuses and the methods herein, can be applied to any appropriate procedure.

Figure 1A:
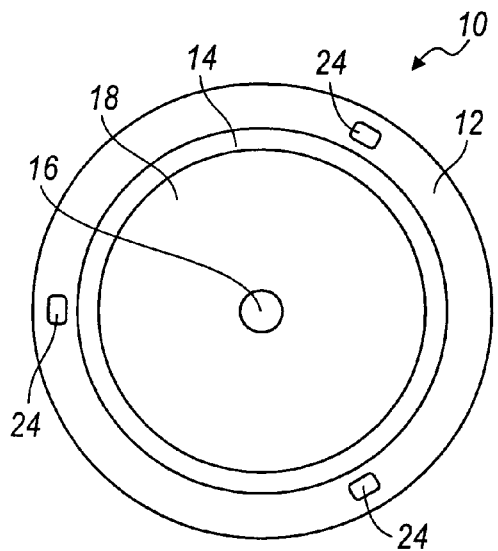
FIG. 1A is a top plane view of an acetabular shell implant according to various embodiments.
Figure 1B:
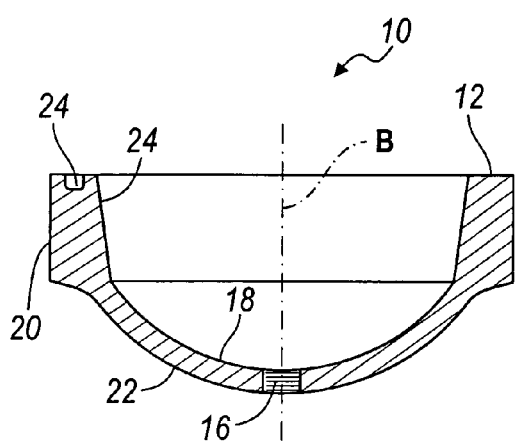
FIG. 1B is a cross-sectional view of the acetabular shell implant of FIG. 1A.
Figure 2:
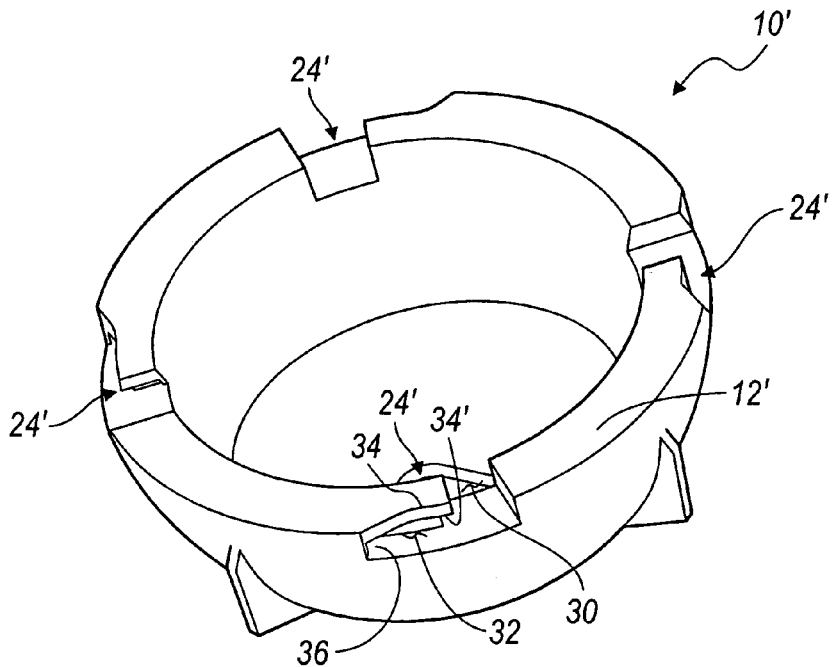
FIG. 2 is a perspective top view of an acetabular shell implant according to various embodiments.
Figure 3A:
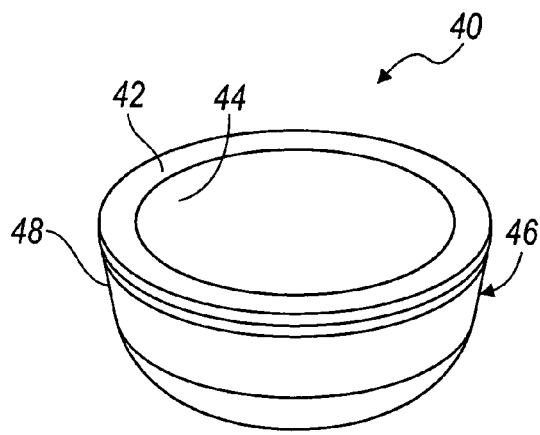
FIG. 3A is a top perspective view of an acetabular liner implant according to various embodiments.
Figure 3B:
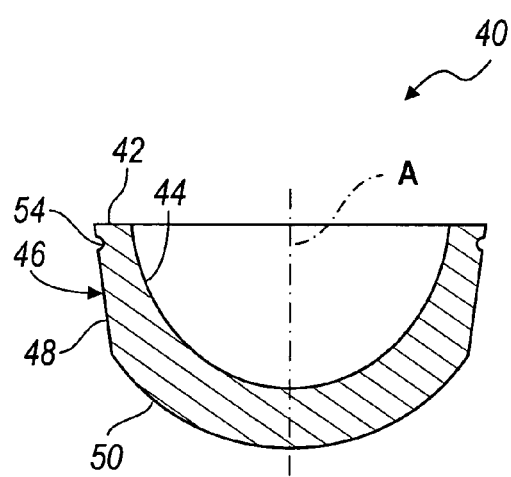
FIG. 3B is a cross-sectional view of the acetabular liner of FIG. 3A.

Initially, with reference to FIGS. 1A-2, an acetabular implant 10 is illustrated. The acetabular implant 10 can be formed of any appropriate material such as titanium, cobalt chromium alloys, stainless steel, or any other appropriate materials. The acetabular implant 10 may include various portions, such as those discussed herein. For example, the acetabular implant 10 can include a rim 12, a tapered inner wall 14, an axial bore 16 and a substantially arcuate inner base. The tapered wall 14 and the arcuate base 18 can be adapted to interact with various portions, such as a liner 40. Further, the acetabular cup 10 can include an exterior upper wall 20 and an outer arcuate base 22. It will be understood that various portions such as anti-rotation fins, spikes, bone in-growth portions and the like can be formed on any of the exterior portions, such as the exterior sidewall 20 or the exterior arcuate base 22. Further, the outer portions may be left substantially smooth to inhibit bone ingrowth for various purposes.

The rim 12 of the acetabular implant 10 can further include various selected portions. For example, markings or alignment portion 24 can be formed in the rim 12, for various purposes such as those discussed herein. The alignment portions 24 can include detents so that a void can be defined in the rim 12 of the acetabular implant 10. It will be understood that any appropriate number of the alignment markers 24 may be provided and the three illustrated are merely an example. Nevertheless, the marking portions 24 can include physical demarcations, such as the physical detents in the rim 12, and/or may include surface demarcations, or any other appropriate portion.

With reference to FIG. 2, an acetabular implant 10' that is similar to the acetabular implant 10 illustrated in FIGS. 1A and 1B can include marker portions 24' according to various embodiments. The marker portions 24' may serve a purpose substantially similar to the marker portions 24 on the acetabular implant 10 of FIGS. 1A and 1B yet can be formed in a different manner. The acetabular implant 10' can include many of the portions substantially similar to the acetabular implant 10. For example, the acetabular implant 10' includes a rim 12' similar to the rim 12 of the acetabular implant 10.

The marker portion 24' is formed in the rim 12' and generally includes a first opening or passage 30. The opening 30 generally traverses a selected depth into the sidewall of the acetabular implant 10' and is substantially the entire width of the rim portion 12'. The opening 30 extends from or interconnects with a slot or undercut area 32. The undercut 32 can be defined in part by an over layer or portion 34 and an end wall 36. The undercut slot 32 can extend from the opening 30 such that a portion that passes through the opening 30 can be moved to the undercut area 32. In this way, a portion that is moved into the undercut area 32 can engage an underside 34' of the over portion 34. A member, such as those described herein, can engage the undercut area 32 for various purposes. Further, the marking portions 24' can be provided on the implant 10' in any appropriate number. Simply, having four marking portions 24' is merely exemplary.

It will be understood that the marker portions 24, 24' are merely exemplary of various marker portions that can be formed on various acetabular cups or shells 10, 10'. Any appropriate marking portion can be used with the markers 24, 24' and those described herein are merely exemplary. Also, the markers portions 24, 24' can be physical engagement portions or simply include visual reference points.

The acetabular shell, according to the various embodiments, can be connected or inserted with an acetabular liner 40. The acetabular or liner 40 can include various portions such as an upper ridge or rim 42. The rim 42 can extend between an inner wall 44 and an outer wall 46. An upper portion of the outer wall 46 can define a taper 48. The taper 48 can extend and interact with a bottom arcuate portion 50. The inner wall 44 can also define an arcuate portion and may be provided in appropriate radii, such as those that can interact with a femoral head.

The acetabular liner 40 can be formed of various materials, such as metals, polymers, ceramics and the like. For example, the acetabular liner 40 can be formed of a selected ceramic material and the taper 48 can be a selected taper to engage the taper defined by the taper wall 14 of the acetabular cup 10, 10'. The respective tapers defined by the acetabular cup taper 14 or the acetabular liner, taper 48, can be any appropriate taper angles. Generally, the taper angles can be about 0.5 degrees to about 30 degrees, such as about 10 degree to about 20 degrees. The various taper angles can be any appropriate taper angle such as those that allow for the acetabular liner 40 to substantially lock in the acetabular cup 10 when the two tapers mate. This can allow the acetabular liner 40 to substantially lock, or at least operably lock in the acetabular shell 10 for use thereof. It will be understood that the operable locking can be a locking that is appropriate for use of the acetabular liner 40 as an anatomical replacement when implanted in an anatomy, such as the human anatomy, yet the acetabular liner 40 can be removed under various circumstances.

Regardless, the taper portion 48 of the acetabular liner 40 generally must be aligned with the taper angle area 14 of the acetabular shell 10. For example, the tapered area 48 can generally be formed as a portion of a cone having a central axis A. Similarly, the acetabular shell 10 can be formed as a portion of a cone having a central axis B. To achieve a selected interaction of the acetabular liner 40 with the acetabular shell 10, it can generally be selected to substantially align the axis A and B as the acetabular liner 40 is driven into or connected with the acetabular shell 10.

Figure 4A:
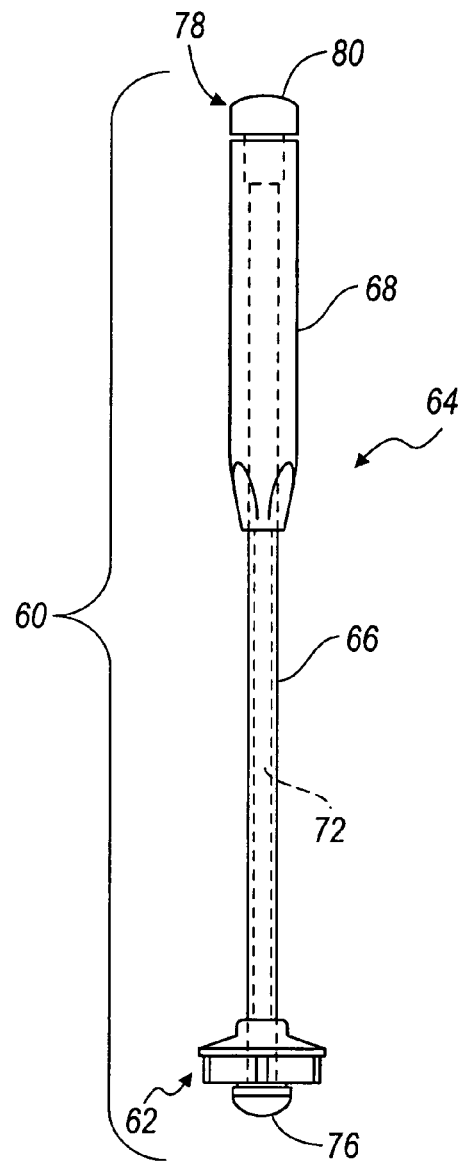
FIG. 4A is a plan view of an acetabular liner inserter according to various embodiments.
Figure 4B:
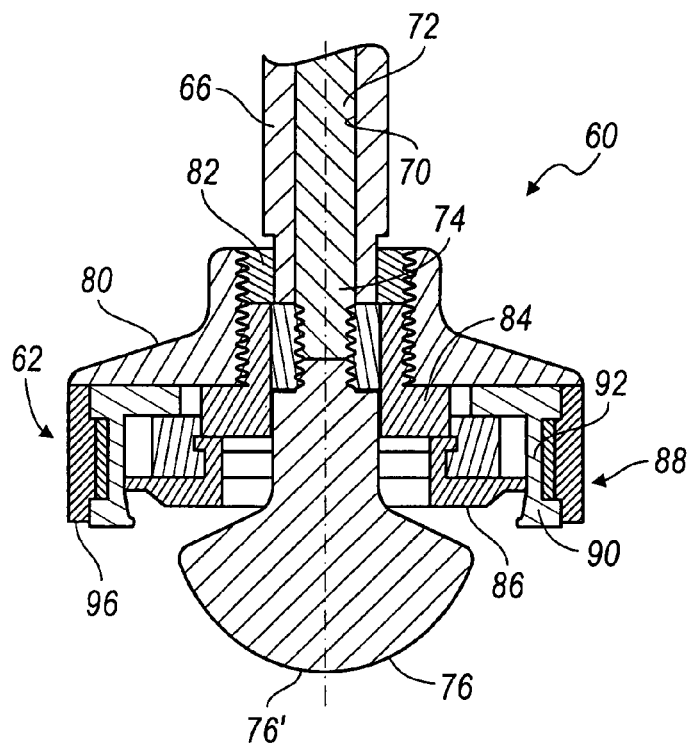
FIG. 4B is a detailed cross-sectional view of an acetabular liner inserter assembly.
Figure 5:
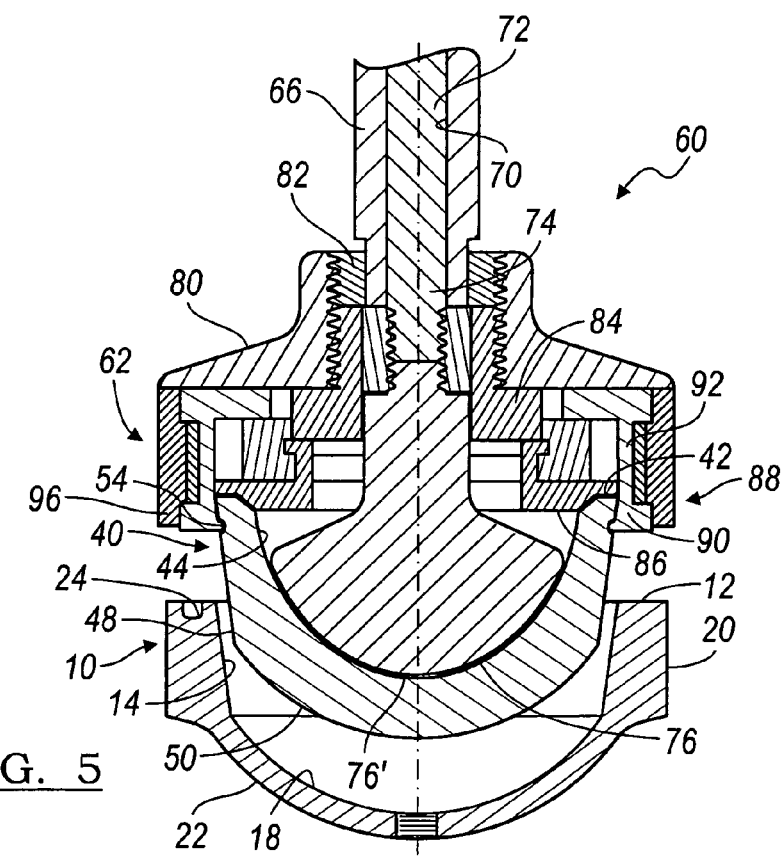
FIG. 5 is a detailed cross-sectional view of an acetabular liner inserter assembly engaged to an acetabular liner and positioned relative to an acetabular shell implant.

The acetabular liner 40 can include connection portions 54 that allow it to be connected with a selected instrument, such as an acetabular liner implanter 60, illustrated in FIGS. 4A-5. The acetabular liner inserter 60 includes an inserter body or assembly 62, a handle shaft assembly 64 including a shaft 66 that extends from the inserter body 62 and a handle 68 that operably engages the shaft 66. The shaft handle assembly 64 can include a cannular bore formed there through, defined by a side wall 70. The side wall 70 can extend through the assembly 64 such that a shaft or rod 72 can extend through the bore.

The rod 72 extends to an engaging end 74 from which a driver 76 can extend from a distal end. Extending from a proximal end of the rod 72 is an impactor end 78. The impactor end 78 can include a member or portion 79 that can be engaged by a hammer or other similar apparatus to drive the acetabular liner 40 into the acetabular cup 10, as described herein.

Figure 4C:
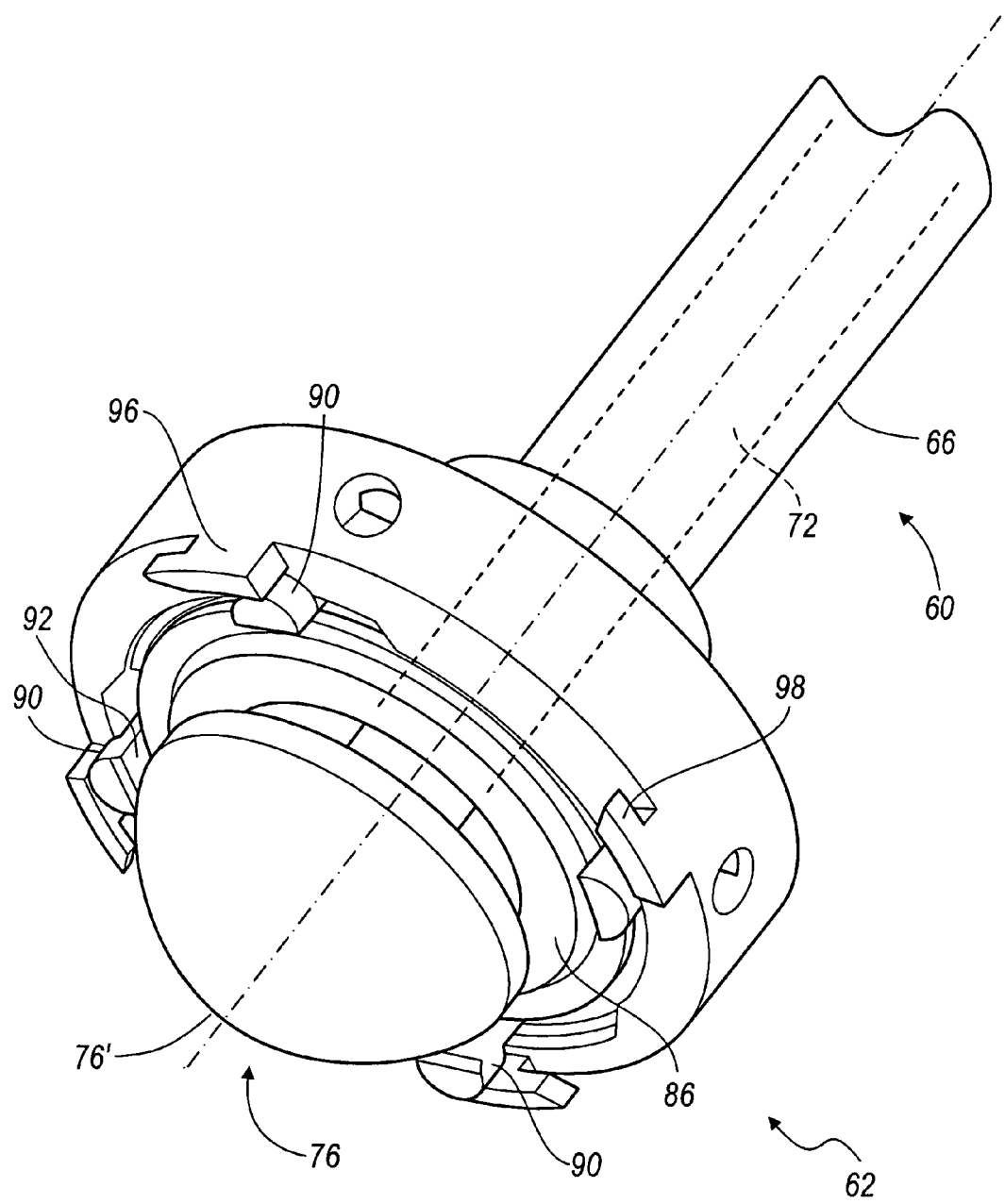
FIG. 4C is a perspective end view of an acetabular liner inserter assembly.

With additional reference to FIGS. 4B and 4C, the acetabular liner inserter 60 can include a plurality of portions defining the inserter body 62. It will be understood that the various portions may also be formed as a single member or integral member or various portions may be formed as single members. Nevertheless, the plurality of members described herein is merely exemplary for forming the acetabular liner inserter 60. As discussed above, the driver 76 can extend from the rod 72 that extends through the shaft 66. The shaft 66 can interconnect with a top plate 80. A plug 82 can be used to extend between the shaft 66 and the top plate 80, but such a plug 82 is not necessary and the shaft 66 can be formed integral with the top plate according to various embodiments. Also interconnected with the top plate 80 is a second spacer or plug 84. The second spacer 84 can further interconnect to the shaft 66 with the inserter body 62 including a seat member 86. Further extending from the top plate 80 are grippers or grip members 88. The grip members 88 can include a grip finger 90 that is operable to move relative to the top plate 80. The grip finger 90 can move in any selected manner relative to the top plate 80 for engaging the acetabular liner 40 as described herein. Further, a spring member can extend from the top plate 80 to engage or assist in manipulating the grip finger 90. As discussed herein, the spring 92 can bias the grip finger 90 in a selected direction, such as inward toward the inserter body 76. The spring 92 can be any appropriate portion and may be formed as a single piece with the grip finger 90.

The inserter body 76 can be formed of any appropriate materials such as a metal, a polymer, or any other selected materials. Generally, the inserter to body 76 can be formed of a material that can insert the acetabular liner 40 without damaging the acetabular liner 40. Therefore, the inserter body 76 can be formed of a selected material that is selected based upon the material from which the acetabular liner 40 is formed. Further, the inserter body 76 can include a distal or engaging end 76' that includes a radius or other shape that is substantially complimentary to the shape of the interior of the acetabular liner 40. In this way, the end 76' of the inserter body 76 can engage a selected amount of the interior surface of the acetabular liner 40 for implanting the acetabular liner 40 into the acetabular shell 10, 10'. It will be understood that the amount that the inserter body 76 engages the acetabular liner 40 can be any selected amount.

Further, the acetabular liner inserter 60 can include an alignment member 96. The alignment member 96 can engage the alignment or marker portions 24, 24' as discussed above and further described herein. It will be understood that the alignment member 96 can include any appropriate portions to engage the various alignment portions 24, 24' of the acetabular shell 10, 10'. Therefore, the alignment member 96 can include a tip or end that is able to engage the detent or depression 24 to allow a user to determine whether a positive engagement has occurred. Further, the alignment portions 96 can include extending fingers or members 98 that may engage the undercut area 32 to engage the under portion 34' of the over layer 34. This can allow the acetabular liner inserter 60 to align or achieve a select alignment with the acetabular shell 10, 10' as discussed further herein.

Figure 4D:
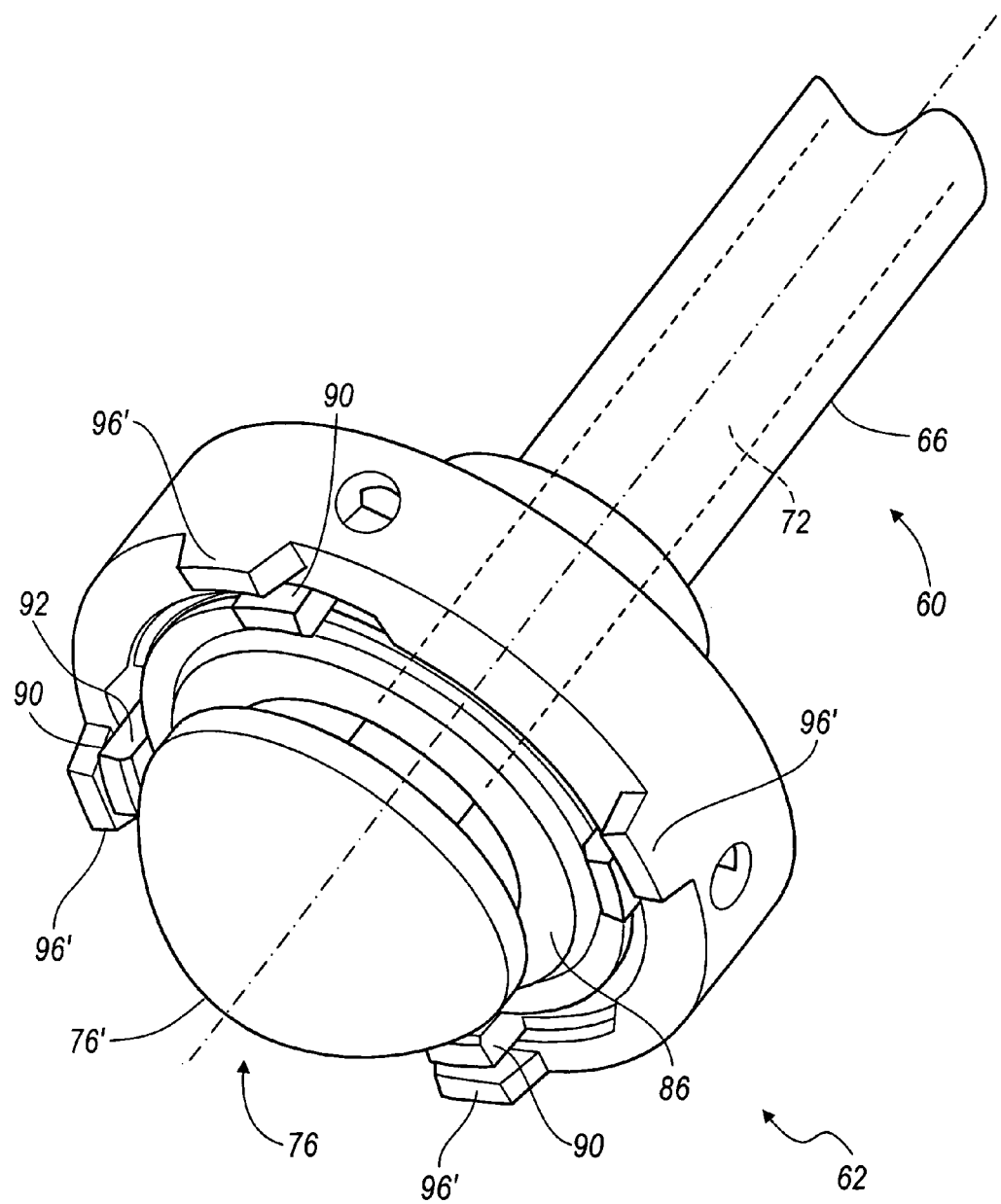
FIG. 4D is a perspective end view of an acetabular liner inserter assembly according to various embodiments.

With reference to FIG. 4D the acetabular liner inserter 60', according to various embodiments, is illustrated. As discussed above the acetabular liner inserter 60' can include the alignment member 96', according to various embodiments. Though the other portions of the acetabular liner inserter 60' can be the same as the other embodiments, the alignment members 96' can be provided to not lock or fixedly engage with the alignment or marker portions 24, 24'. Rather, an engagement can simply include an indication of alignment to a user, rather than locking or holding the acetabular liner inserter 60' to the cup 10, 10' according to various embodiments. Thus, it will be understood that the alignment portions 96, 96' can be provided according to various embodiments, and those illustrated herein are merely exemplary.

With reference to FIG. 5, it is exemplarily illustrated how the acetabular liner inserter 60 can be used to align the acetabular liner 40 with the acetabular shell 10, 10'. The acetabular liner 40 can be engaged with the gripper fingers 90 in the depression 54 defined by the acetabular shell 40. It will be understood that the depression 54 can be a plurality of depressions, an annular depression defined around the acetabular shell 40, or any appropriate engagement point or portion. Regardless, the biased gripper fingers 90 can be biased towards the axis A of the acetabular liner 40 such that the acetabular liner inserter 60 engages the acetabular liner 40 for manipulation thereof. Further, the gripper fingers 90 can allow for manipulation of the acetabular liner 40 in any appropriate manner such as moving through an incision formed in soft tissue in an anatomy, as discussed further herein.

Once the acetabular liner 40 has been appropriately engaged by the acetabular liner inserter 60, the acetabular liner in inserter 60 can be moved relative to the acetabular cup 10, 10' that has been positioned relative to an anatomy, such as that described herein. The alignment portions 96 can engage the alignment portion 24, 24' on the respective acetabular cup 10, 10'. The alignment member 96 can engage the alignment portions 24, 24' in any appropriate manner such as a user is able to determine that the acetabular inserter 60 is aligned relative to the acetabular shell 10, 10'. The engagement can include an audible indication, a touch sensation, or the like to ensure that a user, such as a surgeon, is able to determine, generally intraoperatively, that the acetabular liner inserter 60 is at a selected location orientation relative to the acetabular shell 10, 10'.

As discussed herein, it is generally selected to implant the acetabular liner 40 into the acetabular shell 10, 10' when the axis A is substantially aligned with the axis B to ensure an appropriate interaction of the various taper portions. Therefore, the alignment member 96 can be designed to engage the alignment portions 24, 24' when such an alignment is achieved. This can assist a user in ensuring that the acetabular liner 40 is in a selected orientation prior to forcing or impacting the acetabular liner 40 into the acetabular shell 10, 10'. This can reduce the number of trials necessary to obtain the appropriate orientation of the acetabular liner 40 relative to the acetabular shell 10, 10'.

Once the alignment fingers 96 have been aligned with a selected portion of the acetabular shell 10, 10', the acetabular liner 40 can be disengaged from the acetabular liner inserter 60. The end 80 of the shaft 72 can be engaged in a selected manner, such as with a hand, a tool, or the like to drive the inserter end 76 into the liner 40. The inserter end 76 can include an end 76', that substantially mates with the interior 44 of the acetabular liner 40, so that a force produced with the inserter end can be substantially distributed over the entire surface 44 area. Therefore, the acetabular liner 40 can be inserted into the shell without damaging the surface of the acetabular liner 40. The force of the inserter member 76 pushing against the interior surface 44 of the liner 40 can overcome the biasing force of the spring 92 to disengage the acetabular liner 40 from the gripping fingers 90. Therefore, the acetabular liner 40 can be implanted into the acetabular shell 10, 10' at an appropriate time and after ensuring that an appropriate alignment has been achieved.

It will be understood that the acetabular liner 40 can be centered relative to the acetabular shell 10, 10' in any appropriate procedure. Various procedures may include those described herein or any other selected procedure. For example, the acetabular liner inserter can be used during a substantially less or minimally invasive procedure where an incision is minimized and may be sized merely to allow instruments and implants to pass through. Because the acetabular liner inserter 90 includes the alignment members or portions 96 that allow for a positive feedback when they have engaged the alignment portions 24, 24' visual inspection of the alignment of the acetabular liner 40 relative to the acetabular shell 10, 10' may not be required.

Figure 6:
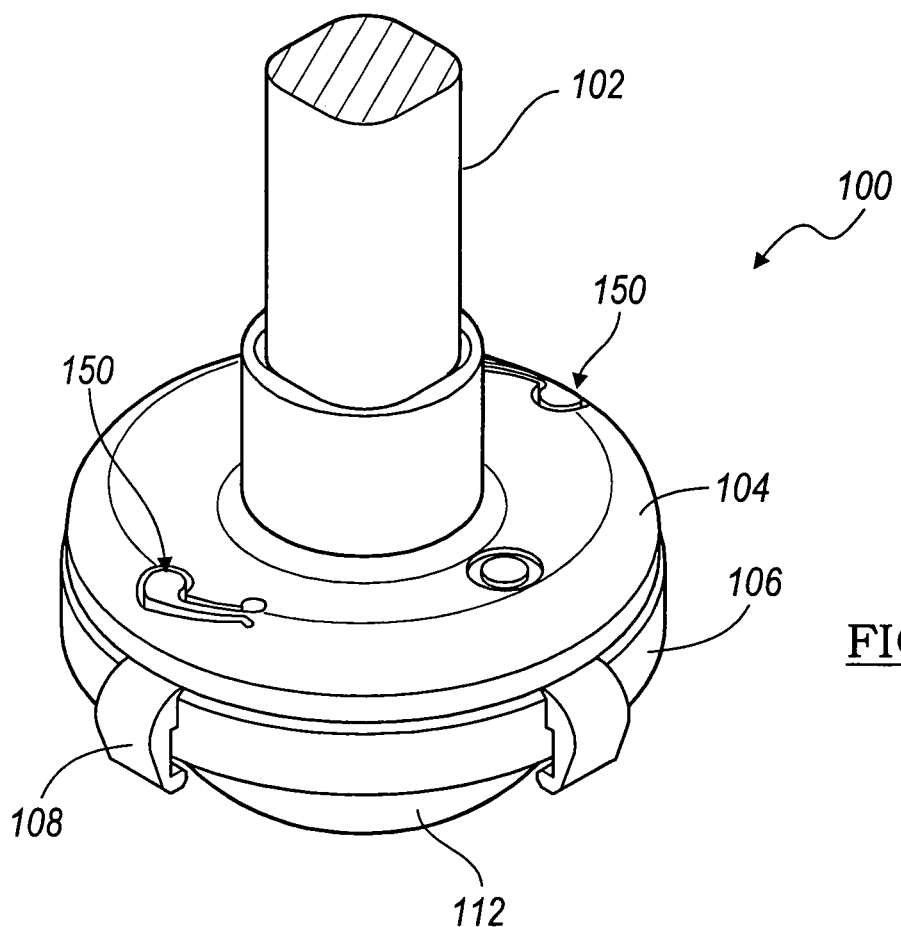
FIG. 6 is a top perspective detailed view of an acetabular shell inserter.
Figure 7:
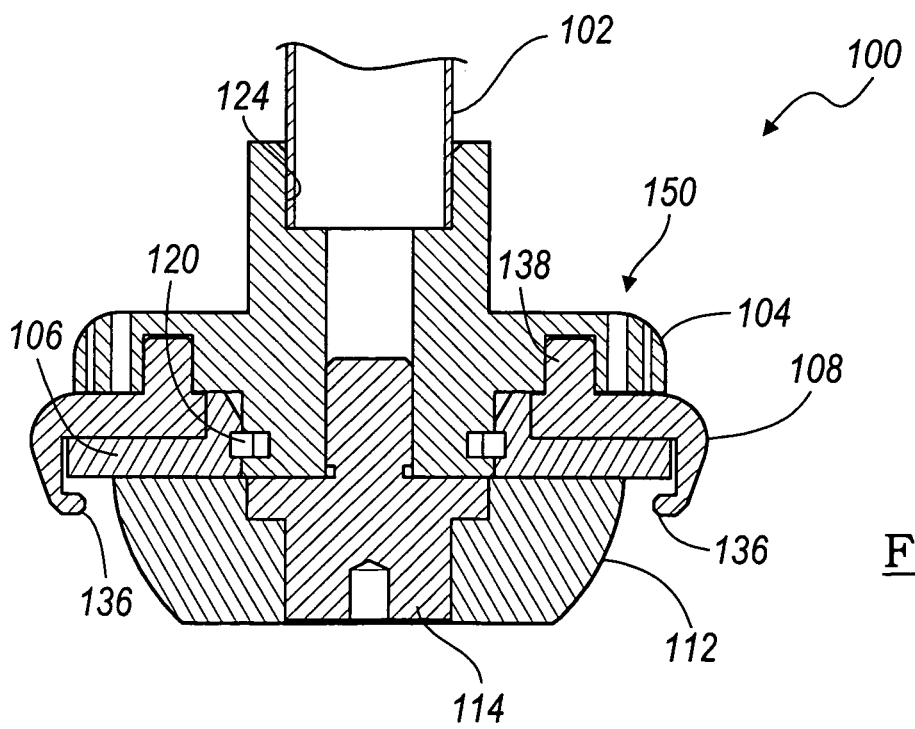
FIG. 7 is a detailed cross-sectional view of an acetabular shell inserter assembly according to various embodiments.

With reference to FIGS. 6-8, a shell inserter assembly 100 is illustrated. It will be understood that the shell inserter assembly 100 can be interconnected with a handle 102 of any appropriate configuration. The handle 102 is able to interact with the shell inserter assembly 100 in an appropriate manner to allow for operation of the shell inserter assembly 100. The shell inserter assembly 100 can be used to insert any appropriate shell, such as the acetabular shell 10. The acetabular shell 10 or any appropriate acetabular shell, can include appropriate portions to allow for interaction with the various portions of the shell inserter 100. Furthermore, the shell can be any appropriate shell and not necessarily the shell or includes all the portions of the shell 10.

The shell inserter assembly 100 generally includes an upper plate 104, a lower plate 106, a locking or manipulatible finger 108. Further, the shell inserter assembly 100 can include a retaining ring or member 120. Further, a dome or plug subassembly 112 can be provided. The dome 112 generally allows for contact with a selected portion of the acetabular shell to be inserted to allow for a large contact surface area to contact the shell for ease of manipulation and distribution of forces relative to the shell.

The various portions of the assembly 100 can be formed of any appropriate materials. For example, the top plate 104, the lower plate 106, the retaining ring 120, and the locking fingers 108 can be formed of various metals or metal alloys. The dome plug 112, however, can be formed of various metal alloys which can be formed of a softer material, such as a polymer, that has a very low likelihood of damaging any materials, such as the acetabular shell.

Initially, the shell inserter assembly 100 can be operated with the handle 102. The acetabular shell can be positioned near the shell inserter assembly 100 and the handle 102 to be manipulated to operate the locking fingers 108. As discussed above, the dome plug 112 can frictionally engage a selected portion of the acetabular shell to allow for movement of the handle 102 without substantially moving the shell inserter assembly 100. The dome plug 112 can be held relative to the upper portions of the assembly 100 with a locking member 114. The locking member 114 can be any appropriate portion, such as including threads to engage an internally threaded portion of the upper plate 104. The dome plug 112 can be held relative to the remaining portions of the shell inserter assembly 100 to allow for a friction engagement between the dome plug 112 and the acetabular shell.

The handle 102, therefore, can be used to rotate the top plate 104 relative to the acetabular shell. The top plate 104 can include various portions that have been formed into the top plate 104 using various methodologies, such as generally known machining techniques, electrical discharge, or the like.

With additional reference to FIG. 8, the top plate 104 can include an upper or proximal portion 120 and a lower or distal portion 122. The handle 102 can engage a handle engaging portion 124 of the top plate 104. The handle engaging portion 124 can be any appropriate portion such as a bore defined by the top plate 104. The handle engaging portion 124 generally can include a cross section that allows for a transfer of torque between the handle 102 and the top plate 104. This can allow for the top plate 104 to rotate when the handle 102 is manipulated.

Further, the top plate can have channels or tracks 126, which can act as cams. The channels 126 can be included in any appropriate number and four channels are illustrated merely for purposes of the present discussion. It will be understood that any appropriate number of the channels 126 can be provided, such as 2, 3, 4, or any appropriate number.

The channel 126 generally includes a first end 128 and a second end 130. The top plate generally defines a central axis or point 132 about which the channel 126 is formed. The first end of 128 of the channel 126 can be formed at a first distance M from the central axis 132. The second end 130 of the channel 126 can be formed at a second distance N from the central axis 132. The difference between the first distance M and the second distance N can be any appropriate amount such as about 0.01 mm to about 10 mm. The distance, however, allows for movement of the locking fingers 108 when a portion of the locking finger 108 is engaged within the channel 126.

The locking finger 108 includes a locking or engagement portion 136 that can be rigidly connected to a guiding portion 138. The guiding portion can be positioned within the channel 126. Thus the top plate 104 can move relative to the locking finger 108 such that the guiding portion 138 is moved within the channel 126. In an initial position, the guiding portion 138 of the locking finger 108 can be positioned near the first end 128 of the channel 126, generally at the distance M from the center 132. Therefore, the engaging portion 136 of the locking finger 108, can be positioned at a maximum distance O from a finger engaging section 140 defined by an acetabular shell 142, as illustrated in FIG. 9A.

The assembly 100 can be pressure engaged such as by holding the acetabular shell 142 against the dome plug 112 and the bottom plate 106 such that the dome 112 and the bottom plate 106 are substantially immobile relative to the acetabular shell 142. Then the handle 102 can be used to rotate the top plate 104 to move the top plate 104 that defines the channels 126. If the top plate 104 rotates, the guiding portion 138 of the locking finger 108 moves in the channel 126 from the first end 128 towards the second end 130. As discussed above, the second end 130 of the channel 126 is closer to the central axis 132 of the shell inserter assembly 100 than the first end 128. Therefore, as the guiding portion 138 moves in the channel 126 towards the second end 130, the locking finger 108 is drawn towards the central axis 132 generally in the direction of arrow P, as illustrated in FIG. 9B. As the locking finger 108 moves generally in the direction of Arrow P towards the central axis 132, it is drawn towards the finger engagement portion 140. The finger engagement portion can be a detent or groove defined by the acetabular shell 142.

Therefore, the rotation of the top plate 104 can move the top plate 104 to move the guiding portion 138 in the channel 126 to draw the locking finger 108 towards the central axis 132 of the top plate 104. The rotation of the top plate 104 can be achieved by pressing the acetabular shell 142 against the dome 112 to form a friction fit between the acetabular shell 142 and the assembly 100. Thus, the rotation of the top plate 104 does not rotate the entire assembly 100. This motion allows for drawing the locking finger 108 towards the acetabular shell 142 to engage a selected portion of the acetabular shell to substantially hold the acetabular shell relative to the shell inserter assembly 100.

The bottom plate 106, or any other appropriate portion of the shell inserter assembly 100, can include various guiding portions. The guiding portions can assist in moving the locking fingers 108 in a substantially linear motion relative to the central axis 132 of the shell inserter assembly 100. The bottom plate 106 can include various tracks or guiding portions that can hold the locking fingers 108 substantially with no angular movement relative to the central axis 132 when the top plate 104 is rotated relative to the dome plug 112. The bottom plate 106, therefore, can assist in ensuring that the locking fingers 108 generally move in the direction of arrow P, and the reverse of arrow P, to hold the acetabular shell 142 in a selected manner.

To further assist in maintaining a selected interconnection between the acetabular shell 142 and the shell inserter assembly 100, a holding assembly or spring 150 can be provided. The holding spring 150 can generally be formed in the top plate 104 using any appropriate method, such as electro discharge, milling, or the like. Generally, the holding spring 150 can include a holding head 152 that is resiliently held in the selected position by a retaining arm 154. The holding head 152 can extend a selected distance into the channel 126. The distance that the holding head 152 extends into the channel 126 can be any appropriate amount, but is generally enough to retain the guiding portion 138 in a selected position until the handle 102 is manipulated with a selected force to resiliently move the holding head 152 to allow the guiding portion 138 to move in the channel 126 to disengage the locking finger 108.

The holding head 152 is generally formed near the second end 130 of the channel 126. As the top plate 104 is rotated relative to the acetabular shell 142, the guiding portion 138 moves in the channel 126 towards the holding head 152 and it can engage a portion of the holding head 152. The engagement of the guiding portion 138 with the holding head 152 can generally move the holding head 152 to allow the guiding pin to pass the holding head 152 to move into a holding position at the second end 130 of the channel 126. The holding head 152 is then resiliently held in the channel 126 with the holding arm 154 so that the guiding portion 138 is held relatively immobile relative to the top plate 104.

This allows the locking finger 108 to be held substantially in the locked or engaged position, as illustrated in FIG. 9B. The holding head 152 allows the locking finger 108 to maintain the engaged position such that a user can manipulate or remove the acetabular shell 142 relative to a selected position while the shell 142 is held relative to the inserter in an appropriate configuration.

Therefore, the shell inserter assembly 100 can be used to engage an acetabular shell, such as the acetabular shell 142, the acetabular shell 10, 10', or any appropriate acetabular shell. The inserter 100, however, can be used to engage an acetabular shell in any appropriate manner to allow for manipulation of the shell by use of the handle 102 for manipulating the inserter 100 while the shell is engaged with the inserter 100. Further, a user, such as a surgeon, can be substantially ensured of an orientation of the shell relative to the shell inserter 100, and therefore, the handle 102 can assist in manipulation and positioning of the shell during a selected procedure, such as an acetabular replacement procedure.

Various instruments, according to various embodiments, have been described above. An exemplary use of the various instruments and portions can include an acetabular replacement during an operative procedure. Although it will be understood that the instruments and portions according to various embodiments can be used for any appropriate procedure, such as a femoral replacement, an acetabular replacement, a glenoid replacement or the like, the following is merely exemplary for understanding an exemplary use of the various embodiments.

With additional reference to FIGS. 10A-11B, and reference to each of the preceding figures, an anatomy 200 can be prepared for implantation of a selected prosthesis. For the present discussion only, the shell 10', the liner 40, and the instruments 60 and 100 will be discussed. It will be understood that the various instruments can be used for any appropriate procedure, and the following discussed procedure is merely exemplary. The anatomy 200 can include a pelvis 202 that defines an acetabulum 204. The acetabulum 204 can be prepared in any appropriate manner, such as those generally known in the art. However, after the acetabulum 204 is prepared, the acetabular implant shell 10' can be positioned relative to the acetabulum 204. Further, a femur 206 can include a femoral head 208 to articulate with a selected portion, such as the liner 40 as discussed herein. It will be understood that the femoral head 208, or any appropriate portion of the femur 206, can also be resected or replaced with selected prostheses. Therefore, it will be understood that the presently disclosed and taught instruments, methods and the like, can be used with any appropriate other prostheses, such as a femoral prosthetic.

An incision 210 can be formed through soft tissue 212 that can include the various portions of soft tissue such as muscle, adipose tissue, dermis, and the like. The incision 210 can include any appropriate dimension, such as a dimension that allows for selected visualization of the acetabulum 204 but minimizing the size of the incision 210. The various instruments, including the liner inserter 60 and the shell inserter 100, such as discussed above, can be used to perform a selected procedure.

Initially, as discussed above, the acetabulum 204 can be prepared. At an appropriate time, the shell 10' can be interconnected with the acetabular shell inserter 100. A method according to various embodiments for interconnecting the acetabular shell inserter 100 with the acetabular shell 10' are discussed above, and not repeated here. Nevertheless, the acetabular inserter 100 can be interconnected with the acetabular shell 10' to allow for manipulation of the shell 10' relative to the prepared acetabulum 204 without substantial visualization of the acetabulum 204.

Figure 10A:
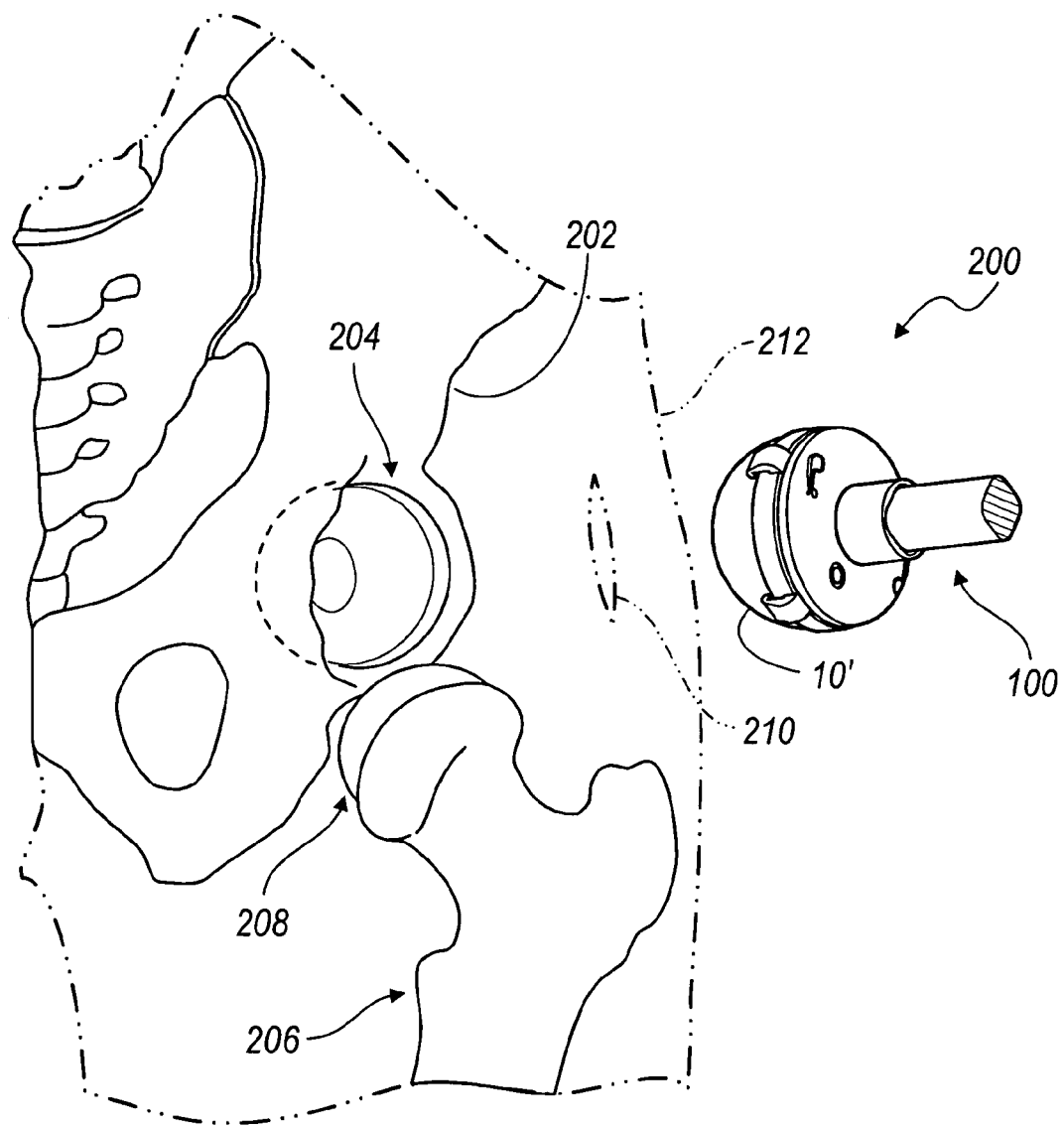
FIG. 10A is an environmental view of an acetabular shell engaged by an acetabular shell inserter relative to an anatomy.
Figure 10B:
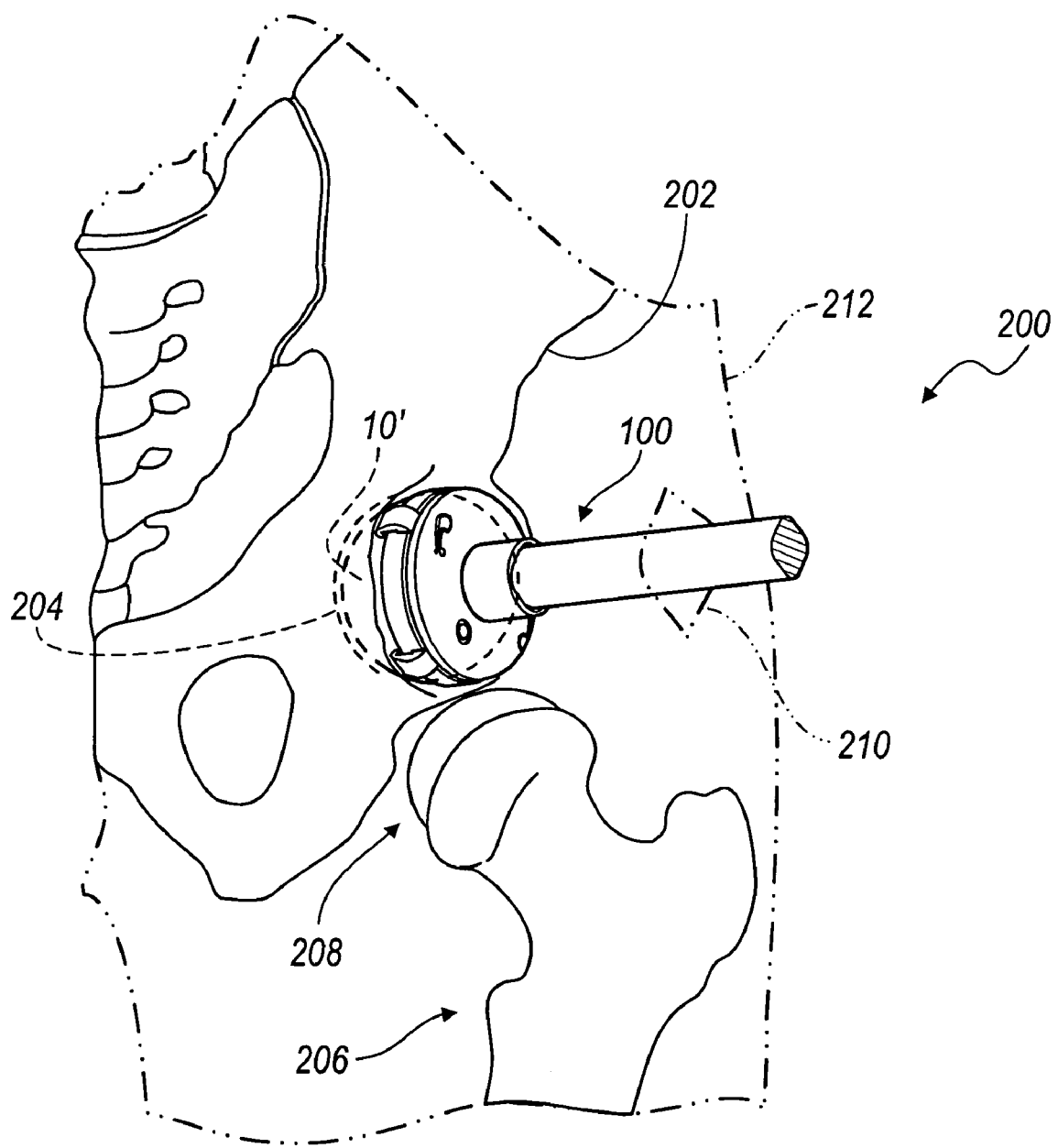
FIG. 10B is an environmental view of an acetabular shell inserter engaging an acetabular shell and positioning it relative to a prepared acetabulum.

With additional reference to FIG. 10B, the acetabular shell inserter 100 can be used to pass the acetabular shell 10' through the incision 210 and relative to the prepared acetabulum 204. The shell inserter 100 can include selected orientation markers that can be used to orientate the acetabular shell 10' relative to the acetabulum 204 in any appropriate manner. It will be understood, according to various embodiments, that the acetabular shell 10' can be implanted relative to the acetabulum 204 in a plurality of appropriate orientations. Further, one skilled in the art will understand that various methods and apparati can be used to orient the acetabular shell 10' relative to the prepared acetabulum 204 in a selected manner. Nevertheless, the acetabular shell inserter 100 can be used to hold the acetabular shell 10' to move it relative to the prepared acetabulum 204 without requiring a plurality of instruments, a large volume of instrumentation, or the like. Therefore, the incision 210 can be maintained at a minimal size to achieve a selected or a minimal invasion during implantation of the acetabular shell 10'.

Figure 11A:
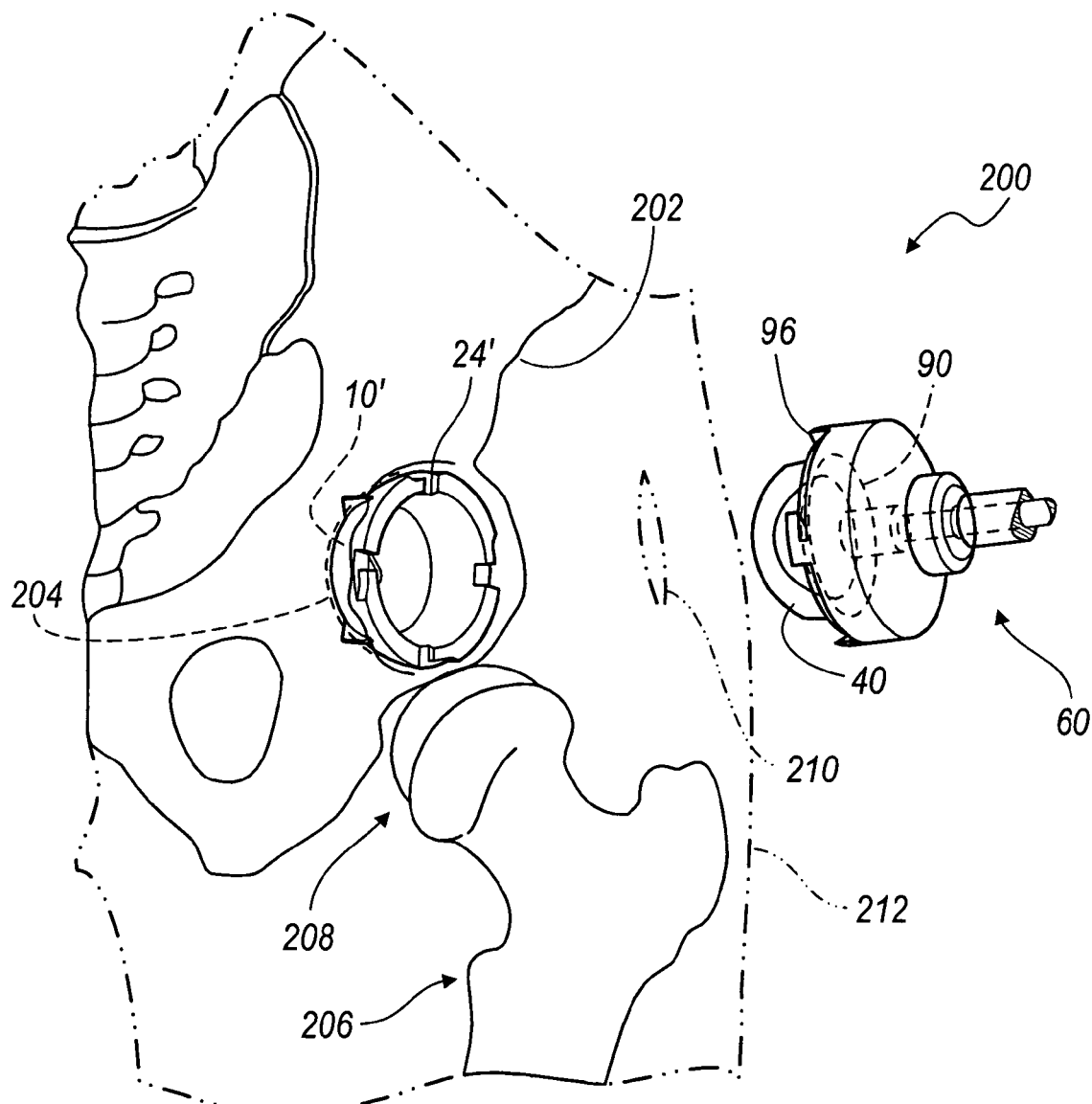
FIG. 11A is an environmental view of an implanted acetabular shell in an acetabular liner inserter assembly engaging an acetabular liner.
Figure 11B:
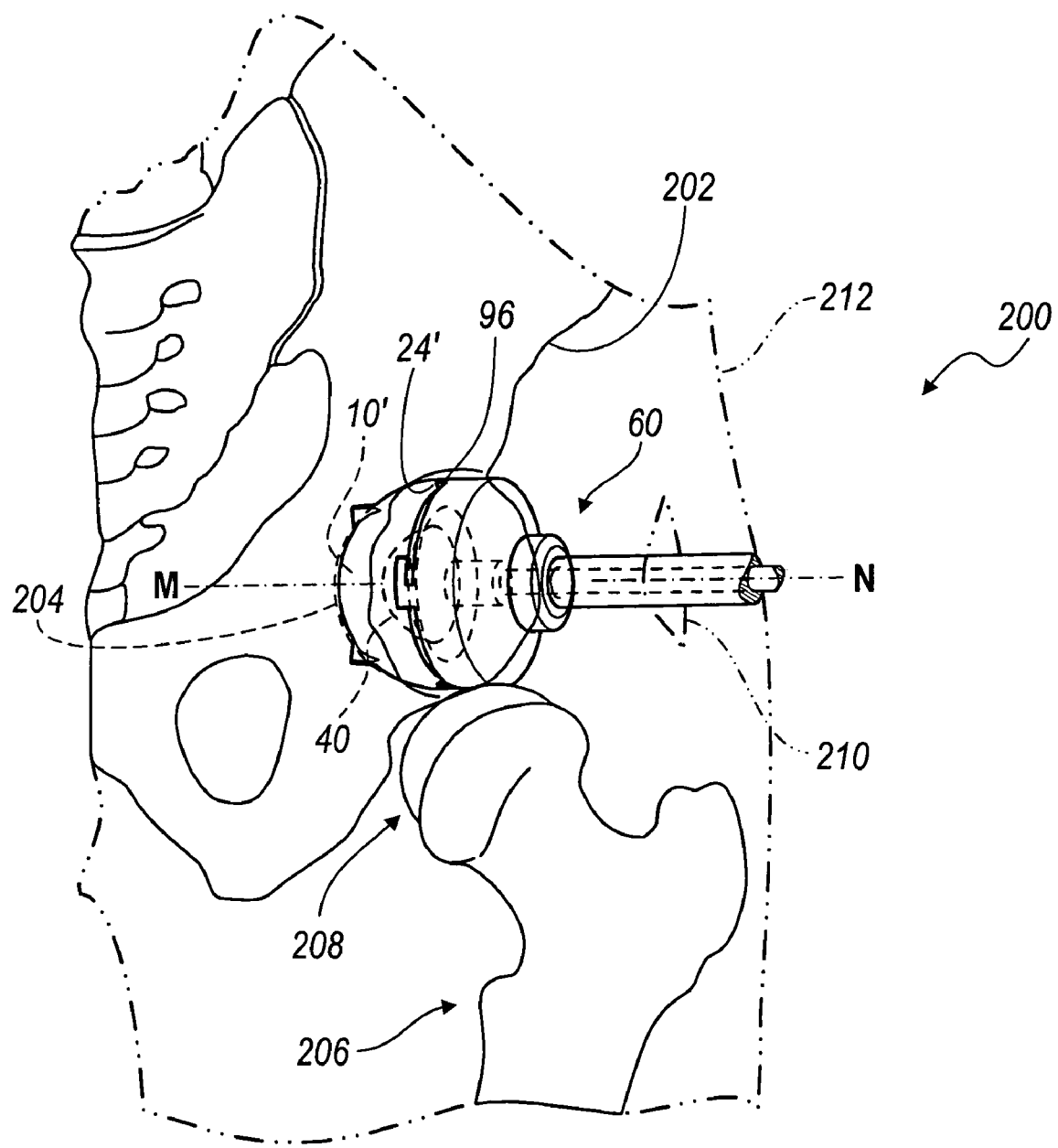
FIG. 11B is an environmental view of an acetabular liner engaged by an acetabular liner inserter and aligned with an axis of an acetabular shell.

With reference to FIG. 11A, once the acetabular shell 10' has been positioned relative to the prepared acetabulum 204 and the pelvis 202, the liner 40 can be moved relative to the implant of acetabular shell 10'. As discussed above, the acetabular shell 40 can be interconnected with the liner inserter 60 in an appropriate manner. Briefly, the retention fingers 90 can engage selected portions of the acetabular liner 40 to hold it relative to the liner inserter instrument 60. The locator fingers 96 can interconnect or engage selected portions, such as the locator portions 24', of the acetabular shell 10' for obtaining a selected orientation of the acetabular liner 40 relative to the acetabular shell 10'. It has been discussed above how the acetabular liner 40 can be interconnected with the acetabular liner inserter 60 and will not be discussed in further detail here, other than to realize that the acetabular liner 40 can be interconnected with the acetabular liner inserter instrument 60 at any appropriate time.

The acetabular liner 40, once it is interconnected with the liner inserter instrument 60, can be moved relative to the incision 210 to move the liner 40 relative to the implanted acetabular shell 10'. The liner inserter instrument 60 can allow for manipulation of the acetabular liner 40 in any appropriate manner to allow for achieving a selected orientation of the acetabular liner 40 relative to the acetabular shell 10'.

The locator fingers 96 can engage the locator elements 24' in any appropriate manner. For example, the liner insert instrument 60 can include the locator fingers 96 that include portions that can engage the undercut area 32 of the acetabular shell 10'. This positive engagement can allow a user to determine that the axis end of the acetabular liner 40 has been appropriately aligned with the axis end of the acetabular shell 10'. Further, a user can determine this without positively or actively viewing the interconnection or position of the liner 40 with the acetabular shell 10'. Because the acetabular liner 40 is originally connected with the acetabular liner inserter 60 and the locator fingers 96 are engaged in the locator portions 24', a user can be assured that the acetabular liner 40 is aligned with the acetabular shell 10' in an appropriate manner.

Once the appropriate alignment has been achieved, the engagement head 80 can be engaged to drive the shaft 72 through the liner inserter 60 to push the acetabular liner 40 to disengage from the engaging fingers 90 with the liner pusher portion 76. This can allow the acetabular liner 40 to be implanted in the acetabular shell 10' in a selected manner.

Therefore, it will be understood that the acetabular liner 40 can be positioned relative to the acetabular shell 10' without vast visualization of the positioning of the two portions. Further, the acetabular liner inserter 60 can interconnect or engage appropriate portions of the acetabular shell 10' to achieve a selected orientation of the acetabular liner 40 with the acetabular shell 10' in a substantially single maneuver. This can reduce trailing the various positions of the implant such as the liner 40 relative to the acetabular shell 10' and can allow for a speedier procedure. It will be understood that the various instruments and implants can be used to achieve any appropriate procedure and implanting an acetabular implant is merely exemplary. Further, any appropriate implant materials can be implanted with the various instruments and methods taught above. Therefore, a ceramic, metal, polyethylene, or the like materials are not required and any appropriate materials can be used to achieve the selected results. Further, the various instruments can allow for positioning of the selected implant prostheses relative to a selected portion of the anatomy or each other without much visualization or with only a minimal amount of visualization yet allowing a successful result.

The description of the teachings are merely exemplary in nature and, thus, variations that do not depart from the gist of the teachings are intended to be within the scope of the teachings. Such variations are not to be regarded as a departure from the spirit and scope of the teachings.

What is claimed is:

1. An implantation system for positioning a prosthesis system relative to a selected portion of an anatomy including a boney portion, the implantation system comprising:
    a shell operable to be positioned relative to the boney portion, the shell including one of an opening and a projection;
    a shell inserter instrument operable to engage an exterior engagement portion of the shell to hold the shell in a selected orientation, the shell inserter instrument having a shell engaging finger extending from a cam follower member that extends into a top plate of the shell inserter instrument, the top plate defines a cam to allow the follower member to move by the cam;
    a liner to engage an interior portion of the shell; and
    a liner inserter instrument to hold the liner in a selected orientation and a shell alignment member to align the shell to orient the liner inserter relative to the shell, the shell alignment member including the other of the opening and the projection, the opening receiving the projection to orient the liner inserter relative to the shell;
    wherein the shell and the liner are operable to be positioned relative to the anatomy;
    wherein the shell includes an exterior wall that defines a detent to be engaged by a shell engaging finger extending from the shell inserter instrument.

2. The implantation system of claim 1, wherein the top plate includes a handle engaging member;
    where a handle is operable to engage the top plate to rotate the top plate to move the cam.

3. The implantation system of claim 1, further comprising:
    a cam follower engaging member operable to hold the cam follower member in a selected position relative to the top plate.

4. The implantation system of claim 1, wherein the shell inserter instrument is operable to be positioned relative to the bony portion through a small incision formed in a portion of the anatomy.

5. The implantation system of claim 1, wherein the shell defines a shell axis and the liner defines a liner axis;

wherein the liner is operably fixed in the shell when the liner is inserted in the shell when the liner axis is aligned with the shell axis.

6. The implantation system of claim 5, wherein the projection is received within the opening to orient the liner relative to the shell so that the liner axis is aligned with the shell axis.

7. The implantation system of claim 6, wherein the liner inserter instrument includes a liner holding member moveable between an engaged position and a non-engaged position;
a biasing member operable to bias the liner holding member in the engaged position.

8. The implantation system of claim 7, wherein the liner inserter instrument further includes a liner disengaging member;
wherein the liner disengaging member moves the liner and assists in moving the liner holding member from the engaged position to the unengaged position and to insert the liner into the shell.

9. The implantation system of claim 1, wherein the shell defines the opening; and wherein the liner inserter instrument includes the projection.

10. The implantation system of claim 9, wherein when the projection is received in the opening, the liner is held by the liner inserter instrument and is aligned with the shell.

11. The implantation system of claim 1, wherein the opening is included on a rim of the shell, and wherein the opening includes an undercut area underneath the rim, the undercut area extending transverse to an axis of the shell, the projection received in the opening and moveable into the undercut area to be coupled to the shell.

12. The implantation system of claim 11, wherein the projection includes an extending finger that extends transverse to an axis of the shell and that is moveable into the undercut area.

13. The implantation system of claim 12, wherein the liner inserter instrument is rotatable about an axis of the shell to move the extending finger into the undercut area.

14. The implantation system of claim 1, wherein the shell includes a rim, and the opening is included on the rim.

15. The implantation system of claim 14, wherein the rim includes an inner edge and an outer edge, and the opening extends from the inner edge to the outer edge.

16. An implantation system for positioning a prosthesis system relative to a selected portion of an anatomy including a boney portion, the implantation system comprising:
a shell operable to be positioned relative to the boney portion;
a shell inserter instrument operable to engage the shell to hold the shell in a selected orientation, the shell inserter instrument including:
a top plate defining a track;
an engagement member including an engagement finger and a cam engaging portion able to be positioned in the track;
a shell contacting portion; and
a handle operable to rotate the top plate to move the engagement member;
a liner to engage an interior portion of the shell; and
a liner inserter instrument to hold the liner in a selected orientation and a shell alignment member to align the shell to orient the liner inserter relative to the shell;
wherein the shell and the liner are operable to be positioned relative to the anatomy;
wherein the top plate defines a central axis;
wherein the track defines a portion of an arc that extends between a first track end and a second track end; and
wherein the first track end is further from the central axis than the second track end.

17. The implantation system of claim 16, wherein the top plate is rotatable relative to the shell contacting portion.

18. The implantation system of claim 16, wherein when the top plate rotates, the cam engaging portion moves within the track between the first track end and the second track end.

19. The implantation system of claim 16, further comprising:
a cam locking member;
wherein the cam locking member is able to lock the cam engaging portion at a selected position relative to the top plate.

20. The implantation system of claim 16, wherein the shell is operable to contact the shell contacting portion so that the handle is operable to rotate the top plate.

21. The implantation system of claim 20, wherein the shell defines an inserter engagement portion;
wherein the engagement finger is operable to engage the inserter engagement portion.

22. The implantation system of claim 16, wherein the shell includes one of an opening and a projection, and wherein the liner inserter includes the other of the opening and the projection, the opening receiving the projection to orient the liner inserter relative to the shell.

23. An implantation system for positioning a prosthesis system relative to a selected portion of an anatomy including a boney portion, the implantation system comprising:
a shell operable to be positioned relative to the boney portion;
a shell inserter instrument operable to engage the shell to hold the shell in a selected orientation, the shell inserter instrument including:
a top plate defining a track;
an engagement member including an engagement finger and a cam engaging portion able to be positioned in the track;
an alignment plate;
a shell contacting portion; and
a handle operable to rotate the top plate to move the engagement member;
a liner to engage an interior portion of the shell; and
a liner inserter instrument to hold the liner in a selected orientation and a shell alignment member to align the shell to orient the liner inserter relative to the shell;
wherein the shell and the liner are operable to be positioned relative to the anatomy;
wherein the alignment plate is positioned between the top plate and the shell contacting portion; and
wherein the alignment plate is operable to guide the engagement finger in a substantially linear motion on a radius relative to the top plate.

24. An implantation system for positioning a prosthesis system relative to a selected portion of the anatomy including a boney portion, the implantation system comprising:
a shell operable to be positioned relative to the boney portion;
a shell inserter instrument operable to engage an exterior engagement portion of the shell to hold the shell in a selected orientation, the shell inserter instrument including:
a top plate defining a track;
an engagement member including an engagement finger and a cam engaging portion able to be positioned in the track;
a shell contacting portion;

a handle operable to rotate the top plate to move the engagement member; and
an alignment plate;
a liner to engage an interior portion of the shell; and
a liner inserter instrument to hold the liner in a selected orientation;
wherein the shell and the liner are operable to be positioned relative to the anatomy; and
wherein the liner inserter instrument includes:
a liner holding body;
a liner engaging member including a finger able to contact the liner and moveable between a contacting position and a non-contacting position;
a biasing member to bias the finger to the contacting position;
a shell alignment member able to align the liner relative to the shell; and
a disengagement member to assist in moving the finger from the contacting position to the non-contacting position;
wherein the alignment plate is positioned between the top plate and the shell contacting portion; and
wherein the alignment plate is operable to guide the engagement finger in a substantially linear motion on a radius relative to the top plate.

25. The implantation system of claim 24, wherein the biasing member includes an arm formed as a single portion with the finger.

26. The implantation system of claim 24, further comprising:
a handle extending from liner holding body;
wherein the handle defines a bore therethrough.

27. The implantation system of claim 26, wherein the disengagement member includes a rod extending through the bore;
a disengagement body extending from the rod;
an activation portion extending from the rod;
wherein the activation portion and the disengagement body generally extend from opposite ends of the rod.

28. The implantation system of claim 27, wherein the activation portion is operable to move the rod and the disengagement body to overcome the biasing force of the biasing member to move the finger.

29. The implantation system of claim 24, wherein the shell includes an alignment portion and wherein the shell alignment member is operable to positively engage the shell alignment portion.

30. The implantation system of claim 24, wherein the shell includes one of an opening and a projection, and wherein liner inserter includes the other of the opening and the projection, the opening receiving the projection to orient the liner inserter relative to the shell.

* * * * *